United States Patent
Akmal et al.

(10) Patent No.: US 12,394,299 B2
(45) Date of Patent: Aug. 19, 2025

(54) USER SUGGESTIONS BASED ON ENGAGEMENT

(71) Applicant: Apple Inc., Cupertino, CA (US)

(72) Inventors: Shiraz Akmal, Playa Vista, CA (US); Aaron M. Burns, Sunnyvale, CA (US); Brad K. Herman, Culver City, CA (US); David A. Carson, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 72 days.

(21) Appl. No.: 18/286,744

(22) PCT Filed: Apr. 12, 2022

(86) PCT No.: PCT/US2022/024491
§ 371 (c)(1),
(2) Date: Oct. 12, 2023

(87) PCT Pub. No.: WO2022/221329
PCT Pub. Date: Oct. 20, 2022

(65) Prior Publication Data
US 2024/0194049 A1    Jun. 13, 2024

Related U.S. Application Data

(60) Provisional application No. 63/174,199, filed on Apr. 13, 2021.

(51) Int. Cl.
*G08B 21/00* (2006.01)
*A61B 5/16* (2006.01)
(Continued)

(52) U.S. Cl.
CPC ............. *G08B 21/182* (2013.01); *A61B 5/16* (2013.01); *G06F 1/163* (2013.01); *G06F 3/016* (2013.01);
(Continued)

(58) Field of Classification Search
CPC ........ G08B 21/182; G16H 50/30; A61B 5/16; G06F 1/163; G06F 3/016; G06F 3/167; G06T 19/006
See application file for complete search history.

(56) References Cited

U.S. PATENT DOCUMENTS 6,763,379 B1 * 7/2004 Shuster ................. H04L 69/329
                                                            709/224
9,141,761 B2 * 9/2015 Lee .......................... G16H 50/30
(Continued)

FOREIGN PATENT DOCUMENTS

DK      180129 B1    6/2020
EP     2729889 A2    5/2014
(Continued)

OTHER PUBLICATIONS

Ask Alexa—Things That Are Smart Wiki, Available online at: <http://thingsthataresmart.wiki/index.php?title=Ask_Alexa&oldid=4283>, Jun. 8, 2016, pp. 1-31.
(Continued)

*Primary Examiner* — Quang Pham
(74) *Attorney, Agent, or Firm* — DLA Piper LLP (US)

(57) ABSTRACT

Systems and processes for operating a digital assistant are provided. An example method includes, at an electronic device having one or more processors and memory, receiving a biometric signature of a user, determining, based on the biometric signature, a wellness level associated with the user, in accordance with a determination that the wellness level associated with the user is below a predetermined threshold, providing a first output to the user to stop engaging with the first electronic device, wherein the first electronic device is capable of producing a virtual environment, and after a predetermined time, causing a second output to
(Continued)

be provided to the user with a second electronic device to begin engaging with the first electronic device.

47 Claims, 7 Drawing Sheets

(51) Int. Cl.

| | |
|---|---|
| *G06F 1/16* | (2006.01) |
| *G06F 3/01* | (2006.01) |
| *G06F 3/16* | (2006.01) |
| *G06T 19/00* | (2011.01) |
| *G08B 21/18* | (2006.01) |
| *G16H 50/30* | (2018.01) |

(52) U.S. Cl.
CPC ............ *G06F 3/167* (2013.01); *G06T 19/006* (2013.01); *G16H 50/30* (2018.01)

(56) References Cited

U.S. PATENT DOCUMENTS

| | | | | |
|---|---|---|---|---|
| 9,378,456 | B2* | 6/2016 | White | G06F 9/4856 |
| 9,628,844 | B2* | 4/2017 | Conrad | H04N 21/44213 |
| 9,681,005 | B2* | 6/2017 | Wang | H04M 19/047 |
| 9,697,822 | B1* | 7/2017 | Naik | G10L 15/22 |
| 10,049,663 | B2* | 8/2018 | Orr | G10L 17/22 |
| 10,798,438 | B2 | 10/2020 | Conrad et al. | |
| 10,818,288 | B2* | 10/2020 | Garcia | G10L 15/22 |
| 10,825,564 | B1* | 11/2020 | Zhang | G06V 40/10 |
| 10,852,905 | B1* | 12/2020 | Guzman | G06F 3/04812 |
| 11,080,336 | B2* | 8/2021 | Van Dusen | G06N 5/02 |
| 11,107,580 | B1* | 8/2021 | Felton | A61B 5/744 |
| 11,216,093 | B2* | 1/2022 | Matsubara | G06F 3/041 |
| 11,250,844 | B2* | 2/2022 | Mont-Reynaud | G10L 15/22 |
| 2008/0090703 | A1* | 4/2008 | Rosenberg | A63B 24/00 |
| | | | | 482/8 |
| 2010/0082376 | A1* | 4/2010 | Levitt | G06Q 10/1093 |
| | | | | 705/7.18 |
| 2011/0083079 | A1* | 4/2011 | Farrell | G06F 3/0237 |
| | | | | 715/780 |
| 2011/0106736 | A1* | 5/2011 | Aharonson | H04M 1/72472 |
| | | | | 706/46 |
| 2013/0151339 | A1* | 6/2013 | Kim | G06Q 30/02 |
| | | | | 705/14.55 |
| 2013/0346068 | A1* | 12/2013 | Solem | G10L 15/26 |
| | | | | 704/9 |
| 2014/0052680 | A1* | 2/2014 | Nitz | G06N 5/04 |
| | | | | 706/46 |
| 2014/0071069 | A1* | 3/2014 | Anderson | A63F 13/42 |
| | | | | 345/173 |
| 2014/0292638 | A1* | 10/2014 | Lee | G06F 3/013 |
| | | | | 345/156 |
| 2014/0310595 | A1* | 10/2014 | Acharya | G06F 3/011 |
| | | | | 715/706 |
| 2014/0340334 | A1* | 11/2014 | Cho | G06F 3/041 |
| | | | | 345/173 |
| 2014/0375551 | A1* | 12/2014 | Oshita | G06F 3/016 |
| | | | | 345/156 |
| 2015/0058720 | A1* | 2/2015 | Smadja | H04L 51/226 |
| | | | | 715/271 |
| 2015/0104043 | A1* | 4/2015 | Takahashi | H04W 56/0005 |
| | | | | 381/119 |
| 2015/0128058 | A1* | 5/2015 | Anajwala | H04L 67/535 |
| | | | | 715/739 |
| 2015/0154291 | A1* | 6/2015 | Shepherd | H04L 67/535 |
| | | | | 707/748 |
| 2015/0248494 | A1* | 9/2015 | Mital | G06F 16/9536 |
| | | | | 707/722 |
| 2015/0293592 | A1* | 10/2015 | Cheong | G06F 1/163 |
| | | | | 345/173 |
| 2015/0317310 | A1* | 11/2015 | Glass | G06F 16/248 |
| | | | | 707/706 |
| 2016/0170477 | A1* | 6/2016 | Flack | G06F 1/3296 |
| | | | | 713/323 |
| 2016/0227897 | A1* | 8/2016 | Jobling | G09F 3/0297 |
| 2016/0249864 | A1* | 9/2016 | Kang | A61B 5/02055 |
| | | | | 340/870.07 |
| 2016/0379105 | A1* | 12/2016 | Moore, Jr. | H04L 67/52 |
| | | | | 706/11 |
| 2017/0000348 | A1* | 1/2017 | Karsten | G06Q 10/1093 |
| 2017/0010669 | A1* | 1/2017 | Lim | G06F 1/163 |
| 2017/0046052 | A1* | 2/2017 | Lee | G06F 3/0488 |
| 2017/0075569 | A1* | 3/2017 | Ward | G06F 1/3296 |
| 2018/0052909 | A1* | 2/2018 | Sharifi | G06F 16/3326 |
| 2018/0109920 | A1* | 4/2018 | Aggarwal | H04W 4/023 |
| 2018/0211345 | A1* | 7/2018 | Bean | G01S 11/06 |
| 2018/0293866 | A1* | 10/2018 | Chung | H04W 64/00 |
| 2018/0367969 | A1* | 12/2018 | Nanjappan | H04W 4/90 |
| 2018/0369616 | A1* | 12/2018 | Dobbing | A62B 18/088 |
| 2019/0025906 | A1* | 1/2019 | Strong | G06F 3/011 |
| 2019/0065993 | A1* | 2/2019 | Srinivasan | G06N 20/00 |
| 2020/0068160 | A1* | 2/2020 | Cho | H04N 21/42204 |
| 2020/0082735 | A1* | 3/2020 | Nel | G06F 3/011 |
| 2020/0379726 | A1 | 12/2020 | Blatz et al. | |
| 2020/0379727 | A1* | 12/2020 | Blatz | G06F 9/451 |
| 2020/0401222 | A1* | 12/2020 | Wisbey | H04R 5/033 |
| 2021/0073293 | A1* | 3/2021 | Fenton | H04L 51/08 |
| 2021/0096646 | A1* | 4/2021 | Yildiz | G06T 19/006 |
| 2021/0217533 | A1* | 7/2021 | Heimerl | A61B 5/7405 |
| 2022/0015717 | A1* | 1/2022 | Ogasawara | G16H 50/20 |
| 2022/0225933 | A1* | 7/2022 | Rehn | H04W 4/90 |

FOREIGN PATENT DOCUMENTS

| | | |
|---|---|---|
| EP | 2915021 A2 | 9/2015 |
| JP | 2015-504619 A | 2/2015 |
| WO | 2009/156978 A1 | 12/2009 |
| WO | 2010/036605 A1 | 4/2010 |
| WO | 2012/160567 A1 | 11/2012 |
| WO | 2013/057153 A1 | 4/2013 |
| WO | 2016/191737 A2 | 12/2016 |

OTHER PUBLICATIONS

Dwork et al., "The Algorithmic Foundations of Differential Privacy", Foundations and Trends in Theoretical Computer Science: vol. 9: No. 3-4, 211-407, 2014, 281 pages.

Hutsko et al., "iPhone All-in-One For Dummies", 3rd Edition, Dec. 31, 2013, 98 pages.

Lin Luyuan, "An Assistive Handwashing System with Emotional Intelligence", Using Emotional Intelligence in Cognitive Intelligent Assistant Systems, 2014, 101 pages.

Rowland et al., "Designing Connected Products: UX for the Consumer Internet of Things", O'Reilly, May 31, 2015, 452 pages.

Sullivan Danny, "How Google Instant's Autocomplete Suggestions Work", available at <http://searchengineland.com/how-google-instant-autocomplete-suggestions-work-62592>, Apr. 6, 2011, 12 pages.

Tur et al., "The CALO Meeting Assistant System", IEEE Transactions on Audio, Speech, and Language Processing, vol. 18, No. 6, Aug. 2010, pp. 1601-1611.

International Preliminary Report on Patentability received for PCT Patent Application No. PCT/US2022/024491, mailed on Oct. 26, 2023, 11 pages.

International Search Report and Written Opinion received for PCT Patent Application No. PCT/US2022/024491, mailed on Jul. 26, 2022, 15 pages.

* cited by examiner

USER SUGGESTIONS BASED ON ENGAGEMENT

CROSS REFERENCE TO RELATED APPLICATIONS

This application is a U.S. National Stage Patent Application of PCT Application No. PCT/US2022/024491, entitled "USER SUGGESTIONS BASED ON ENGAGEMENT," filed on Apr. 12, 2022, which claims the benefit of U.S. Provisional Application No. 63/174,199, entitled "USER SUGGESTIONS BASED ON ENGAGEMENT," filed Apr. 13, 2021. The contents of each of these applications are hereby incorporated by reference in their entireties.

FIELD

This relates generally to digital assistants and, more specifically, to monitoring user engagement and providing suggestions based on user engagement with a digital assistant.

BACKGROUND

Intelligent automated assistants (or digital assistants) can provide a beneficial interface between human users and electronic devices. Such assistants can allow users to interact with devices or systems using natural language in spoken and/or text forms. For example, a user can provide a speech input containing a user request to a digital assistant operating on an electronic device. The digital assistant can interpret the user's intent from the speech input and operationalize the user's intent into tasks. The tasks can then be performed by executing one or more services of the electronic device, and a relevant output responsive to the user request can be returned to the user.

In some cases, users may interact with digital assistants within virtual and augmented reality settings in such a comprehensive manner that the user may neglect to monitor their own wellness and thus cannot determine when they should take a break from interacting with the digital assistant and/or electronic device. Accordingly, efficient ways for the digital assistant to monitor the user's wellness level and prompt the user to take a break may be desirable. It may further be desired for the digital assistant to provide a reminder of the user to end the break and engage with the digital assistant again to increase the user's productivity and level of engagement.

SUMMARY

Example methods are disclosed herein. An example method includes, at an electronic device having one or more processors and memory, receiving a biometric signature of a user, determining, based on the biometric signature, a wellness level associated with the user, in accordance with a determination that the wellness level associated with the user is below a predetermined threshold, providing a first output to the user to stop engaging with the first electronic device, wherein the first electronic device is capable of producing a virtual environment, and after a predetermined time, causing a second output to be provided to the user with a second electronic device to begin engaging with the first electronic device.

Example non-transitory computer-readable media are disclosed herein. An example non-transitory computer-readable storage medium stores one or more programs. The one or more programs include instruction for receiving a biometric signature of a user, determining, based on the biometric signature, a wellness level associated with the user, in accordance with a determination that the wellness level associated with the user is below a predetermined threshold, providing a first output to the user to stop engaging with the first electronic device, wherein the first electronic device is capable of producing a virtual environment, and after a predetermined time, causing a second output to be provided to the user with a second electronic device to begin engaging with the first electronic device.

Example electronic devices are disclosed herein. An example electronic device comprises one or more processors; a memory; and one or more programs, where the one or more programs are stored in the memory and configured to be executed by the one or more processors, the one or more programs including instructions for receiving a biometric signature of a user, determining, based on the biometric signature, a wellness level associated with the user, in accordance with a determination that the wellness level associated with the user is below a predetermined threshold, providing a first output to the user to stop engaging with the first electronic device, wherein the first electronic device is capable of producing a virtual environment, and after a predetermined time, causing a second output to be provided to the user with a second electronic device to begin engaging with the first electronic device.

An example electronic device comprises means for receiving a biometric signature of a user, means for determining, based on the biometric signature, a wellness level associated with the user, in accordance with a determination that the wellness level associated with the user is below a predetermined threshold, means for providing a first output to the user to stop engaging with the first electronic device, wherein the first electronic device is capable of producing a virtual environment, and means for after a predetermined time, causing a second output to be provided to the user with a second electronic device to begin engaging with the first electronic device.

Determining, based on the biometric signature, a wellness level associated with the user allows a digital assistant to monitor whether a user is efficiently interacting with the digital assistant and any chosen tasks being completed by the digital assistant. Accordingly, the digital assistant may determine whether a user would benefit from a break in engagement with the digital assistant and therefore more efficiently use their time. This in turn increases the efficiency of the digital assistant and any electronic device running the digital assistant as less time is wasted by the user repeating tasks they are not engaged with. This allows the digital assistant to provide tasks when the user is engaged rather than repeatedly performing a task over and over when a user is distracted, reducing the power consumption of the digital assistant and improving the battery life of the electronic device.

DESCRIPTION

Figure 1A:
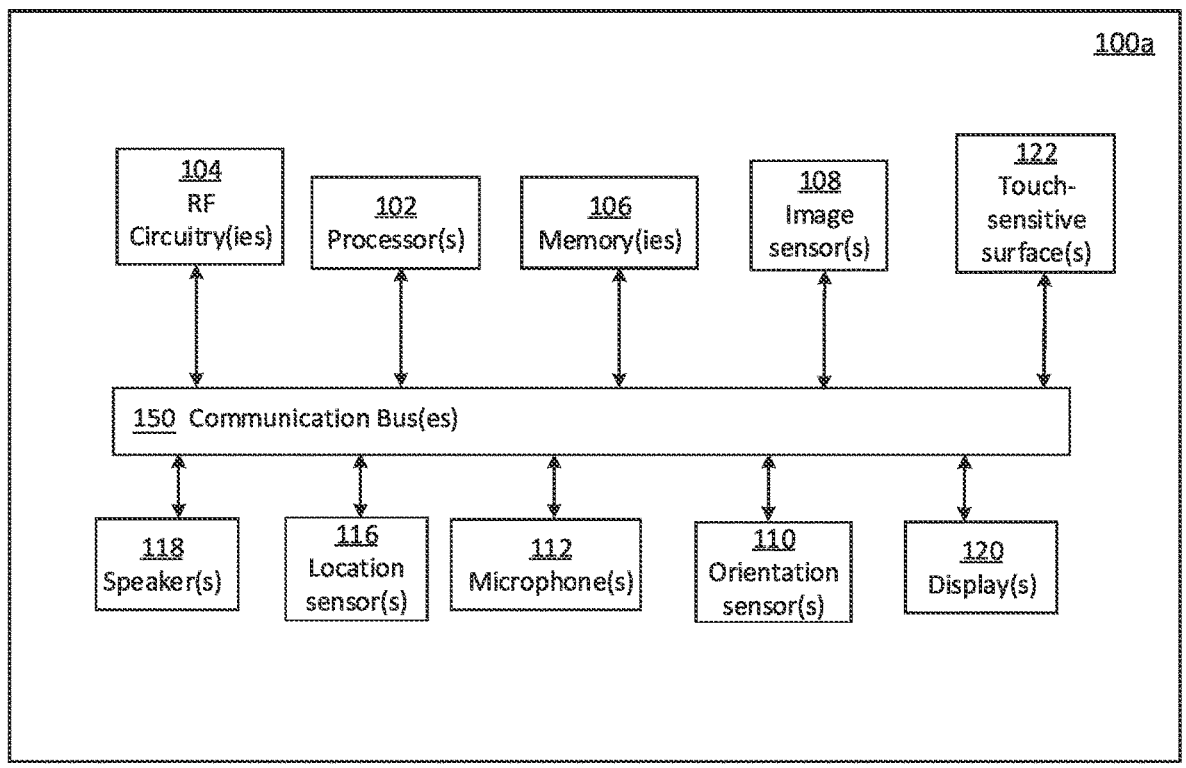
FIGS. 1A-1B depict exemplary systems for use in various computer-generated reality technologies, including virtual reality and mixed reality.

People may sense or interact with a physical environment or world without using an electronic device. Physical features, such as a physical object or surface, may be included within a physical environment. For instance, a physical environment may correspond to a physical city having physical buildings, roads, and vehicles. People may directly sense or interact with a physical environment through various means, such as smell, sight, taste, hearing, and touch. This can be in contrast to an extended reality (XR) environment that may refer to a partially or wholly simulated environment that people may sense or interact with using an electronic device. The XR environment may include virtual reality (VR) content, mixed reality (MR) content, augmented reality (AR) content, or the like. Using an XR system, a portion of a person's physical motions, or representations thereof, may be tracked and, in response, properties of virtual objects in the XR environment may be changed in a way that complies with at least one law of nature. For example, the XR system may detect a user's head movement and adjust auditory and graphical content presented to the user in a way that simulates how sounds and views would change in a physical environment. In other examples, the XR system may detect movement of an electronic device (e.g., a laptop, tablet, mobile phone, or the like) presenting the XR environment. Accordingly, the XR system may adjust auditory and graphical content presented to the user in a way that simulates how sounds and views would change in a physical environment. In some instances, other inputs, such as a representation of physical motion (e.g., a voice command), may cause the XR system to adjust properties of graphical content.

Numerous types of electronic systems may allow a user to sense or interact with an XR environment. A non-exhaustive list of examples includes lenses having integrated display capability to be placed on a user's eyes (e.g., contact lenses), heads-up displays (HUDs), projection-based systems, head mountable systems, windows or windshields having integrated display technology, headphones/earphones, input systems with or without haptic feedback (e.g., handheld or wearable controllers), smartphones, tablets, desktop/laptop computers, and speaker arrays. Head mountable systems may include an opaque display and one or more speakers. Other head mountable systems may be configured to receive an opaque external display, such as that of a smartphone. Head mountable systems may capture images/video of the physical environment using one or more image sensors or capture audio of the physical environment using one or more microphones. Instead of an opaque display, some head mountable systems may include a transparent or translucent display. Transparent or translucent displays may direct light representative of images to a user's eyes through a medium, such as a hologram medium, optical waveguide, an optical combiner, optical reflector, other similar technologies, or combinations thereof. Various display technologies, such as liquid crystal on silicon, LEDs, uLEDs, OLEDs, laser scanning light source, digital light projection, or combinations thereof, may be used. In some examples, the transparent or translucent display may be selectively controlled to become opaque. Projection-based systems may utilize retinal projection technology that projects images onto a user's retina or may project virtual content into the physical environment, such as onto a physical surface or as a hologram.

Figure 1B:
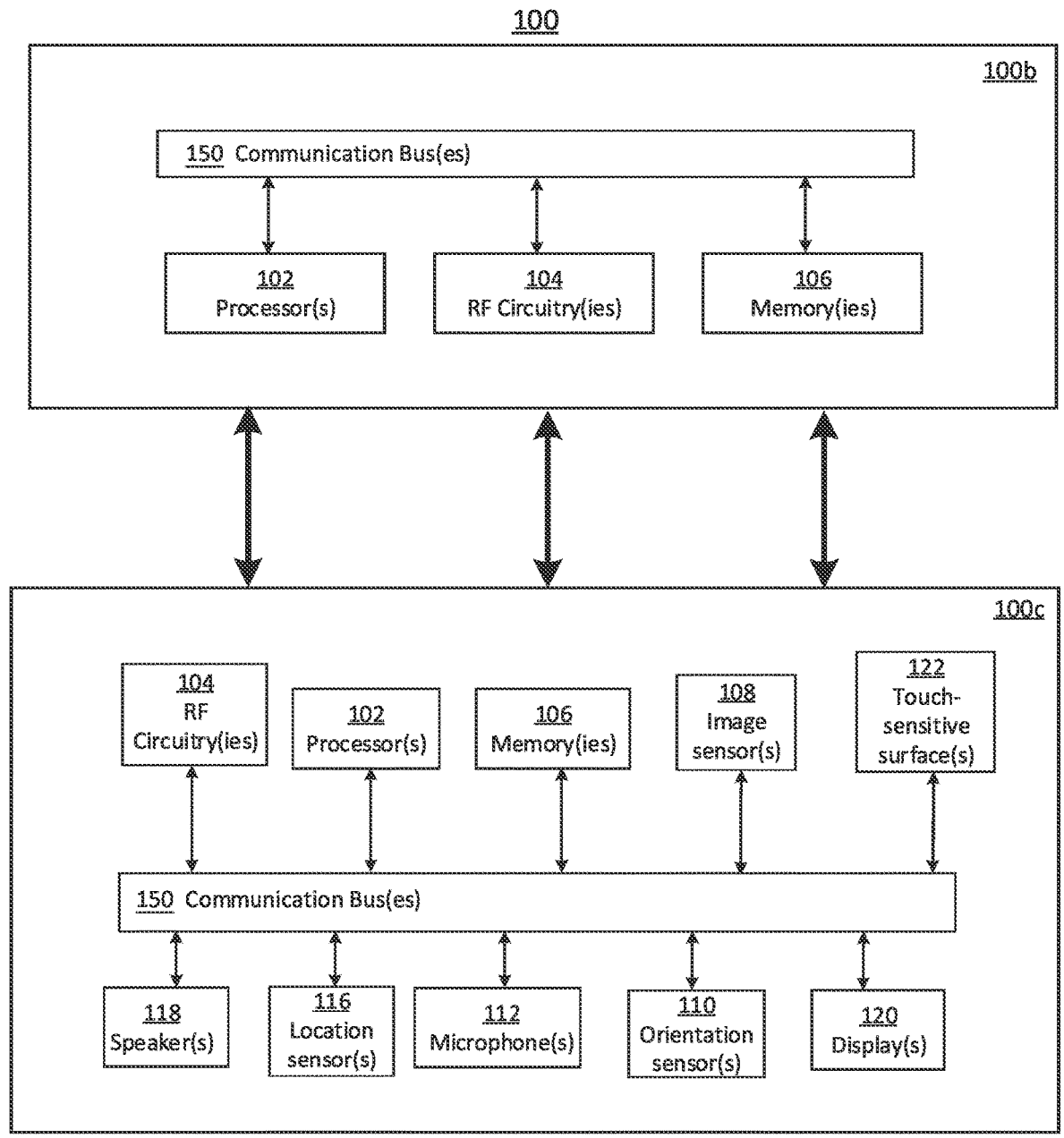

FIG. 1A and FIG. 1B depict exemplary system 100 for use in various extended reality technologies.

As shown in FIG. 1A, system 100 includes device 100*a*. Device 100*a* includes RF circuitry(ies) 104, processor(s) 102, memory(ies) 106, image sensor(s) 108, touch-sensitive surface(s) 122, speaker(s) 118, location sensor(s) 116, microphone(s) 112, orientation sensor(s) 110, and display(s) 120. These components optionally communicate using communication bus(es) 150 of device 100*a*.

In some examples, a base station device (e.g., a computing device, such as a remote server, mobile device, or laptop) implements some components of system 100 and a second device (e.g., a head-mounted device) implements other components of system 100. In some examples, device 100*a* is implemented in a base station device or in a second device.

As shown in FIG. 1B, in some examples, system 100 includes two or more devices in communication, e.g., via a wired connection or a wireless connection. First device 100*b* (e.g., a base station device) includes memory(ies) 106, RF circuitry(ies) 104, and processor(s) 102. Such components optionally communicate using communication bus(es) 150 of device 100*b*. Second device 100*c* (e.g., a head-mounted device) includes components such as RF circuitry(ies) 104, processor(s) 102, memory(ies) 106, image sensor(s) 108, touch-sensitive surface(s) 122, speaker(s) 118, location sensor(s) 116, microphone(s) 112, orientation sensor(s) 110, and display(s) 120. These components optionally communicate using communication bus(es) 150 of device 100*c*.

System 100 includes RF circuitry(ies) 104. RF circuitry(ies) 104 optionally include circuitry for communicating with networks (e.g., the Internet, a wireless network (e.g., such as cellular networks and wireless local area networks (LANs)), and/or intranets) and/or electronic devices. RF circuitry(ies) 104 optionally includes circuitry for communicating using near-field communication and/or short-range communication (e.g., Bluetooth®).

System 100 includes processor(s) 102 and memory(ies) 106. Processor(s) 102 include one or more graphics processors, one or more general processors, and/or one or more digital signal processors. In some examples, memory(ies) 106 are one or more non-transitory computer-readable storage mediums (e.g., random access memory, flash memory) storing computer-readable instructions configured to be executed by processor(s) 102 to perform the techniques described below.

System 100 includes image sensor(s) 108. Image sensors(s) 108 optionally include one or more infrared (IR) sensor(s), e.g., a passive IR sensor or an active IR sensor, to detect infrared light from the physical environment. For example, an active IR sensor includes an IR emitter (e.g., an IR dot emitter) for emitting infrared light into the physical environment. Image sensor(s) 108 also optionally include one or more visible light image sensors, such as complementary metal-oxide-semiconductor (CMOS) sensors and/or charged coupled device (CCD) sensors capable of obtaining images of physical elements from the physical environment. Image sensor(s) 108 also optionally include one or more event camera(s) configured to capture movement of physical elements in the physical environment. Image sensor(s) 108 also optionally include one or more depth sensor(s) capable of detecting the distance of physical elements from system 100. In some examples, system 100 uses IR sensors, CCD sensors, event cameras, and depth sensors together to detect the physical environment around system 100. In some examples, image sensor(s) 108 include first and second image sensors. The first and second image sensors are optionally capable of capturing images of physical elements in the physical environment from two respective different perspectives. In some examples, system 100 uses image sensor(s) 108 to detect the position and orientation of system 100 and/or display(s) 120 in the physical environment. For example, system 100 uses image sensor(s) 108 to track the position and orientation of display(s) 120 relative to one or more fixed elements in the physical environment. In some examples, image sensor(s) 108 are capable of receiving user inputs, such as hand gestures.

In some examples, system 100 includes touch-sensitive surface(s) 122 for receiving user inputs, such as tapping or swiping inputs. In some examples, touch-sensitive surface(s) 122 and display(s) 120 are combined into touch-sensitive display(s).

In some examples, system 100 includes microphones(s) 112. System 100 uses microphone(s) 112 to detect sound from the user's physical environment or from the user. In some examples, microphone(s) 112 includes a microphone array (e.g., including a plurality of microphones) that optionally operate together, e.g., to locate the spatial source of sound from the physical environment or to identify ambient noise.

System 100 includes orientation sensor(s) 110 for detecting orientation and/or movement of system 100 and/or display(s) 120. For example, system 100 uses orientation sensor(s) 110 to track changes in the position and/or orientation of system 100 and/or display(s) 120, such as relative to physical elements in the physical environment. Orientation sensor(s) 110 optionally include gyroscope(s) and/or accelerometer(s).

System 100 includes display(s) 120. Display(s) 120 may operate with a transparent or semi-transparent displays (and optionally with one or more imaging sensors). Display(s) 120 may include an opaque display. Display(s) 120 may allow a person to view a physical environment directly through the display, and may also allow addition of virtual content to the person's field of view, e.g., by superimposing virtual content over the physical environment. Display(s) 120 may implement display technologies such as a digital light projector, a laser scanning light source, LEDs, OLEDs, liquid crystal on silicon, or combinations thereof. Display(s) 120 can include substrates through which light is transmitted, e.g., optical reflectors and combiners, light waveguides, holographic substrates, or combinations thereof. As a particular example, the transparent or semi-transparent display may selectively transition between a transparent or semi-transparent state and an opaque state. Further example implementations of display(s) 120 include display-capable lenses, tablets, smartphones, desktop computers, laptop computers, heads up displays, display-capable automotive windshields, or display-capable windows. In some examples, system 100 is a projection-based system. For example, system 100 projects virtual objects onto a physical environment (e.g., projects a holograph onto a physical environment or projects imagery onto a physical surface). As another example, system 100 uses retinal projection to project images onto a person's eyes (e.g., retina). In some examples, system 100 can be configured to interface with an external display (e.g., a smartphone display).

Figure 2:
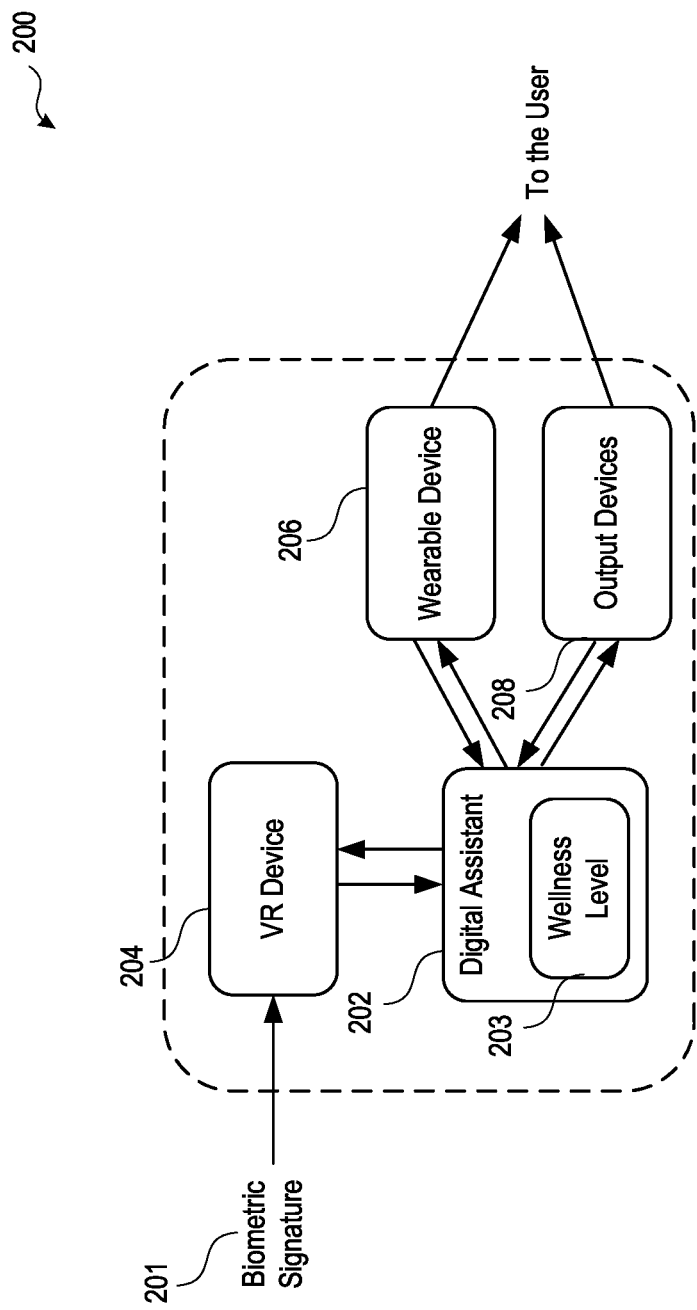
FIG. 2 depicts an exemplary system for monitoring a user wellness level and providing user suggestions, according to various examples.

FIG. 2 depicts exemplary system 200 for monitoring a user wellness level and providing user suggestions, according to various examples. In some examples, as illustrated in FIG. 2, system 200 includes digital assistant 202, VR device 204, wearable electronic device 206, and output devices 208. In some examples, these components of system 200 may optionally be combined as discussed further below. In some examples, digital assistant 202 is implemented on one or more of the devices included in system 200, such as VR device 204, wearable electronic device 206, and/or output devices 208. In some examples, digital assistant 202 is implemented across other devices (e.g., a server) in addition to the devices depicted in system 200. In some examples, some of the modules and functions of the digital assistant are divided into a server portion and a client portion, where the client portion resides on one or more user devices (e.g., electronic device 100, VR device 204, wearable electronic device 206, and output devices 208) and communicates with the server portion through one or more networks.

It should be noted that system 200 is only one example of such a system, and that system 200 can have more or fewer devices than shown, can combine two or more devices, or can have a different configuration or arrangement of the devices. Digital assistant 202 is implemented in hardware, software instructions for execution by one or more processors, firmware, including one or more signal processing and/or application specific integrated circuits, or a combination thereof. In some examples, digital assistant 202 connects to one or more components and/or sensors of VR device 204, wearable electronic device 206, and output devices 208 as discussed further below.

System 200 uses the various devices depicted, including VR device 204, wearable electronic device 206, and output devices 208 to monitor the wellness level of users of system 200 to determine whether the user should take a break and thus whether system 200 should provide the user with an output to stop engaging with system 200. Additionally, system 200 may use the various devices to provide other outputs or reminders to the user, including prompts to re-engage with system 200 (or a specific device of system 200) when certain criteria is met (e.g., after the user has taken a break, when the user has an event scheduled, or when the user will be productive).

While the user is engaged with VR device 204, system 200 and in particular VR device 204 of system 200 receives biometric signature 201 of the user. Biometric signature 201 includes one or more biometric signals that can represent a wellness level of the user including the pulse of the user, the blood pressure of the user, an attention level of the user, an eye pattern of the user, a facial pattern (e.g., facial expressions) of the user, a voice pattern of the user, an electroencephalogram (EEG) of the user, or a temperature of the user. Biometric signature 201 is received by one or more sensors of VR device 204 including one or more cameras, a thermometer, a heart rate sensor, one or more microphones, one or more electrodes etc.

For example, while the user is wearing VR device 204 (e.g., a VR headset), a camera of VR device 204 that is pointed in the direction of the user face may monitor the user's eyes to determine an eye pattern of the user. As another example, while the user is wearing VR device 204, earpieces or a strap that is used to hold VR device 204 may include a heart rate sensor and/or a thermometer that may measure the user's pulse or temperature respectively.

In some examples, biometric signature 201 includes multiple biometric signatures received by multiple different sensors of VR device 204. For example, biometric signature 201 may include the eye pattern of the user determined by an interior camera of VR device 204, the temperature of the user determined by a thermometer of VR device 204, a voice pattern of the user received by a microphone of VR device 204, and the pulse of the user received by a heart rate sensor of VR device 204.

In some examples, biometric signature 201 is received by one or more sensors of wearable device 206 or output devices 208 and is provided to VR device 204 or another electronic device (e.g., a server) for further processing by digital assistant 202. For example, when wearable device 206 is a smart watch, wearable device 206 may measure the pulse of the user with a heart rate monitor included in the smart watch and provide the pulse of the user to VR device 204 as biometric signature 201.

After receiving biometric signature 201, VR device 204 provides biometric signature 201 to digital assistant 202 which determines wellness level 203 associated with the user based on biometric signature 201. Digital assistant 202 can be implemented on VR device 204 and thus use the various components of VR device 204 (e.g., memory, processors, etc.) to determine wellness level 203. In some examples, digital assistant 202 is implemented on a server as well as VR device 204 and thus uses the components of VR device 204 and the server (e.g., memory, processors, etc.) to determine wellness level 203.

In some examples, wellness level 203 includes a score determined based on biometric signature 201. Thus, digital assistant 202 may assign a numerical value to each of the biometric signatures received as part of biometric signature 201 and average them to determine an overall wellness level of the user. For example, when biometric signature 201 includes a pulse of the user and an eye pattern of the user, digital assistant 202 may assign a numerical value to the pulse of the user based on whether it is considered to be a normal level, a high level, etc. and also assign a numerical value to the eye pattern of the user based on whether the user's eye pattern is erratic. Thus, if the user's pulse is over 100 (e.g., 110, 115, 125, 145, etc.) a lower numerical value may be assigned to the user's pulse indicating that the user is likely not well. Similarly, if the user's eye pattern is very erratic (e.g., looking at many different objects and directions) a lower numerical value may be assigned to the user's eye pattern also indicating that the user is likely not well. Averaging these two numbers would thus result in a low value for wellness level 203, indicating that the user has a low overall wellness level.

In contrast, if the user's pulse is below 100 (e.g., 80, 85, 90, etc.) a higher numerical value may be assigned to the user's pulse indicating that the user is likely well. Similarly, if the user's eye pattern is not very erratic (e.g., focusing on a single object, document, etc.) a higher numerical value may be assigned to the user's eye pattern indicating that the user is likely well. Averaging these two numbers would thus result in a high value for wellness level 203, indicating that the user has a high overall wellness level.

In some examples, wellness level 203 is based on one or more interactions between the user and VR device 204. Interactions between the user and VR device 204 include opening new tasks or windows, looking away from a primary task, adjusting a setting of VR device 204, etc. Interactions such as those described above can indicate that the user is losing focus and may have been engaged with VR device 204 for longer than generally desired, resulting in a lower wellness level. Accordingly, digital assistant 202 may determine a relatively low wellness level 203 (or adjust wellness level 203 to be lower) when the user has interacted with VR device 204 in this manner.

In some examples, wellness level 203 is based on contextual data associated with the user. Exemplary contextual data associated with user includes an amount of time the user has been engaged with VR device 204, one or more scheduled events associated with the user, a user profile associated with the user, or other information associated with the user that digital assistant 202 has access to. Accordingly, when determining wellness level 203 digital assistant 202 may consider this contextual data to calculate or adjust the score.

For example, contextual data associated with the user may indicate that the user has been engaged with VR device 204 for several hours and that the user has a virtual meeting scheduled an hour from the current time. Digital assistant 202 may then determine or adjust wellness level 203 to be lower to indicate that the user should take a break, even if biometric signal 201 indicates that the user is generally well.

In some examples, wellness level 203 is based on contextual data associated with VR device 204. Contextual data associated with VR device 204 may indicate a location of the VR device 204 (e.g., GPS coordinates), whether VR device 204 is connected to a network (e.g., WiFi network), whether VR device 204 is connected to one or more other devices (e.g., headphones), and/or a current time, date, and/or weekday. If the VR device 204 is connected to a network or device, the contextual data may further indicate a name and/or type of the network or device, respectively. Accordingly, when determining wellness level 203 digital assistant 202 may consider this contextual data to calculate or adjust the score.

For example, contextual data associated with VR device 204 may indicate that the current location of VR device 204 is a public park and that VR device 204 is not connected to a WiFi network. Accordingly, digital assistant 202 may determine that the user is in a good location to take a break and thus determine (or adjust) wellness level 203 to be lower to indicate that the user should take a break, even if biometric signal 201 indicates that the user is generally well.

Contextual data associated with VR device 204 may further include a number of applications open, the types of applications that are open, or specific objects/data provided by the open applications. Accordingly, digital assistant 202 may further determine or adjust wellness level 203 based on this application data. For example, contextual data associated with VR device 204 may indicate that the user has ten different applications open and that all of the applications are sharing different, unrelated objects or data. Based on this, digital assistant 202 may determine (or adjust) wellness level 203 to be lower to indicate the user should take a break because the contextual data indicates that the user may be overwhelmed, even if this is not reflected in biometric signal 201.

Contextual data associated with VR device 204 may further include whether one or more other devices of system 200 (e.g., wearable device 206 and output devices 208) is present at the current location of VR device 204 or is actively connected to VR device 204. For example, contextual data associated with VR device 204 may indicate that one or more output devices 208 (e.g., a smart speaker) is present at the current location of VR device 204. Accordingly, digital assistant 202 may determine that it is a good time for the user to take a break because the user may be reminded to re-engage later with output device 208, as described further below. Thus, digital assistant 202 may adjust wellness level 203 to be lower to encourage the user to take a break from engaging with VR device 204.

Wellness level 203 is also based on whether a virtual environment is currently being provided by VR device 204.

For example, if VR device 204 is currently providing a virtual environment, digital assistant 202 may weight some factors such as how long the user has been interacting with VR device 204 more heavily. In particular, currently providing a virtual environment combined with a long use time may indicate that the user has not taken a break recently and thus digital assistant 202 may adjust wellness level 203 accordingly.

In some examples, wellness level 203 is based on contextual data associated with other devices of system 200 such as wearable device 206 and output devices 208. Contextual data associated with wearable device 206 and output devices 208 is similar to contextual data associated with VR device 204 and may indicate a location of the electronic device (e.g., GPS coordinates), whether the electronic device is connected to a network (e.g., WiFi network), whether the electronic device is connected to one or more other devices (e.g., headphones), and the presence of one or more other devices of system 204. Thus, as discussed above, digital assistant 202 may recognize that because the user is near other devices of system 200 the user is more likely to respond to a reminder from one of those devices and it is a good time for the user to take a break.

After determining wellness level 203, digital assistant 202 determines whether wellness level 203 is below a predetermined threshold. The predetermined threshold is a threshold that indicates whether the user is currently well or not well. For example, the threshold may be any number that can indicate the boundary between the user being well or not well based on wellness level 203. Accordingly, the predetermined threshold may be any real number such as 50, 60, 75, 95, 100, etc.

It will be understood that while a determination that wellness level 203 is below a predetermined threshold is described herein, system 200 and digital assistant 202 could also determine whether wellness level 203 is above a predetermined threshold or at a predetermined threshold and perform further actions as described below based on this determination. Thus, system 200 is not constrained to only determinations that wellness level 203 is below the predetermined threshold and may include flexible determinations depending on when the user would like to be notified or if someone other than the user, such as a medical professional, would like to be notified based on a particular wellness level. Moreover, system 200 may include custom notifications for specific wellness levels or specific biometric signatures that the user or a medical professional may find helpful or interesting.

In some examples, the predetermined threshold is determined based on one or more default threshold values. For example, default values may be provided by a panel of doctors or other experts that indicate when a user is generally healthy or well and thus does not need to take a break from engaging with VR device 204. Thus, these values provided (determined) by the experts can be applied to system 200 as the predetermined threshold to show when the user is well or unwell.

In some examples, the predetermined threshold is determined based on one or more baseline biometric signatures associated with the user. In some examples, the one or more baseline biometric signatures associated with the user are determined based on previous interactions between the user and VR device 204. For example, as the user interacts with VR device 204, digital assistant 202 may record biometric signature 201. This may occur for many different instances of interaction between the user and VR device 204 so that digital assistant 202 determines a biometric signature for the user when they are well rested and thus at an appropriate baseline.

In some examples, the one or more baseline biometric signatures associated with user are determined based on a setup process of VR device 204 and/or digital assistant 202. For example, when the user first uses VR device 204, digital assistant 202 may prompt the user through a setup process in which digital assistant 202 asks the user to provide various biometric signatures such as pulse, temperature, voice signature, etc. These biometric signatures may then be stored as baseline biometric signatures and used to determine the predetermined threshold or be modified over time as discussed above.

In some examples, the one or more baseline biometric signatures associated with user are stored in a user profile associated with the user that can be accessed by digital assistant 202. For example, as discussed above, when the user provides baseline biometric signatures while setting up VR device 204 the baseline biometric signatures may be stored in a user profile associated with the user. The user profile may then be updated with new biometric signatures over time to provide a more accurate baseline biometric signature. In some examples the user profile may exist prior to setting up VR device 204 and the baseline biometric data may be added to the prior existing user profile. In some examples, the user profile may be created when the baseline biometric data is determined (e.g., during set up of VR device 204).

Figure 3:
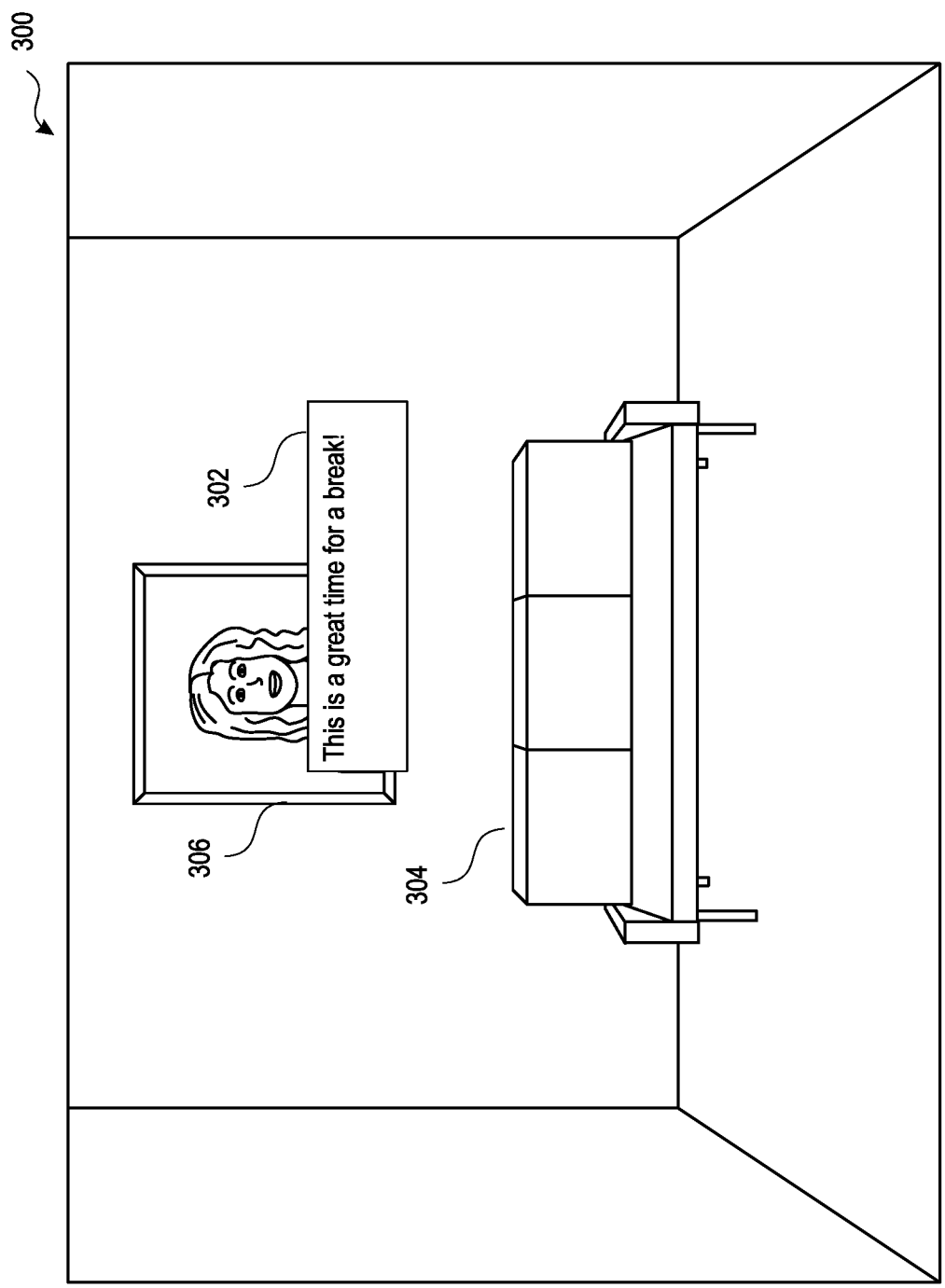
FIG. 3 depicts an exemplary output of the system for monitoring the user wellness level.

When digital assistant 202 determines that wellness level 203 is below the predetermined threshold, digital assistant 202 provides an output (e.g., a first output) to the user to stop engaging with VR device 204. In some examples, the output to stop engaging with VR device 204 includes a visual prompt within a provided virtual environment, as shown in FIG. 3. Accordingly, digital assistant 202 can provide prompt 302 including "This is a great time for a break!" within virtual environment 300 that includes various virtual objects including virtual objects 304 and 306. In this way, the user's interaction with VR device 204 is interrupted by the prompt.

In some examples, VR device 204 may detect an input dismissing prompt 302 such as a virtual swipe of prompt 302 or an audio input of "I'll take a break in a little while." In response to detecting the input dismissing prompt 302, digital assistant 202 may dismiss prompt 302 and restore virtual environment 300 so that the user may continue interacting with VR device 204. In some examples, after dismissing prompt 302, digital assistant 202 may forgo providing the prompt for a predetermined time (e.g., 10, 15, 30, or 45 minutes) and then provide the prompt again. In some examples, after dismissing prompt 302, digital assistant 202 may forgo providing the prompt until wellness level 203 is again determined to be below the predetermined threshold.

In some examples, the output to stop engaging with VR device 204 includes haptic feedback. For example, VR device 204 may provide an output to the user to stop engaging with VR device 204 with a vibration in addition to or instead of providing prompt 302 discussed above. In some examples, the haptic feedback is provided with a second device of system 200 such as wearable device 204. For example, when wearable device 204 is a smart watch, digital assistant 202 may cause wearable device 204 to provide the haptic feedback rather than or in addition to the prompt provided by VR device 204.

In some examples, the output to stop engaging with VR device 204 (e.g., the first output) is determined based on one or more user settings. For example, the user may indicate that they prefer to be prompted via an audio output rather than a visual indicator as shown in FIG. 3. Accordingly, when digital assistant 202 determines that an output should be provided to the user, digital assistant 202 will provide the output as an audio output. In some examples, the one or more user settings are stored in the user profile associated with the user. For example, the information indicating that the user prefers audio outputs may be stored in the user profile associated with the user along with other data such as the baseline biometric signatures discussed above. In some examples the output to stop engaging with VR device 204 is a default type, such as providing the visual prompt within the virtual environment.

After providing the output to stop engaging with VR device 204, digital assistant 202 waits a predetermined time and then causes a second output to be provided to the user with another electronic device of system 200 (e.g., wearable device 206 or output devices 208). Accordingly, the second output is a prompt for the user to again engage with VR device 204 and the virtual environment provided by VR device 204.

In some examples, the predetermined time is based on one or more user settings. For example, the user may specify that they want their breaks to last a specific amount of time such as 10, 20, 30, 45, or 60 minutes. Accordingly, the user may change the length of the break and thus the predetermined time so that the second output is delivered when the user prefers. In some examples, the predetermined time is default amount of time, such as 15 minutes.

In some examples, the predetermined time is based on contextual data associated with the user and/or devices of system 200. As discussed above contextual data associated with the user includes an amount of time the user has been engaged with VR device 204, one or more scheduled events associated with the user, a user profile associated with the user, or other information associated with the user that digital assistant 202 has access to. Further, contextual data associated with the devices of system 200 includes whether the devices are connected to a network, the time of day, the date, the location of the device etc. Thus, digital assistant 202 may determine or adjust the predetermined time based on one or more of the contextual data discussed above.

For example, contextual data associated with the user may indicate that the user has a meeting in an hour at the user's office while contextual data associated with VR device 204 may indicate that VR device 204 is connected to a home network associated with the user. Accordingly, digital assistant 202 may determine that the user is located at home and needs to be at their office in an hour. Accordingly, digital assistant 202 may set the predetermined time as a length of time required for the user to get to the user's office in time for the meeting, such as 30 minutes. Thus, digital assistant 202 may provide the second output to the user after 30 minutes so that the user re-engages with VR device 204 at that time and is reminded of their upcoming meeting.

Figure 4:
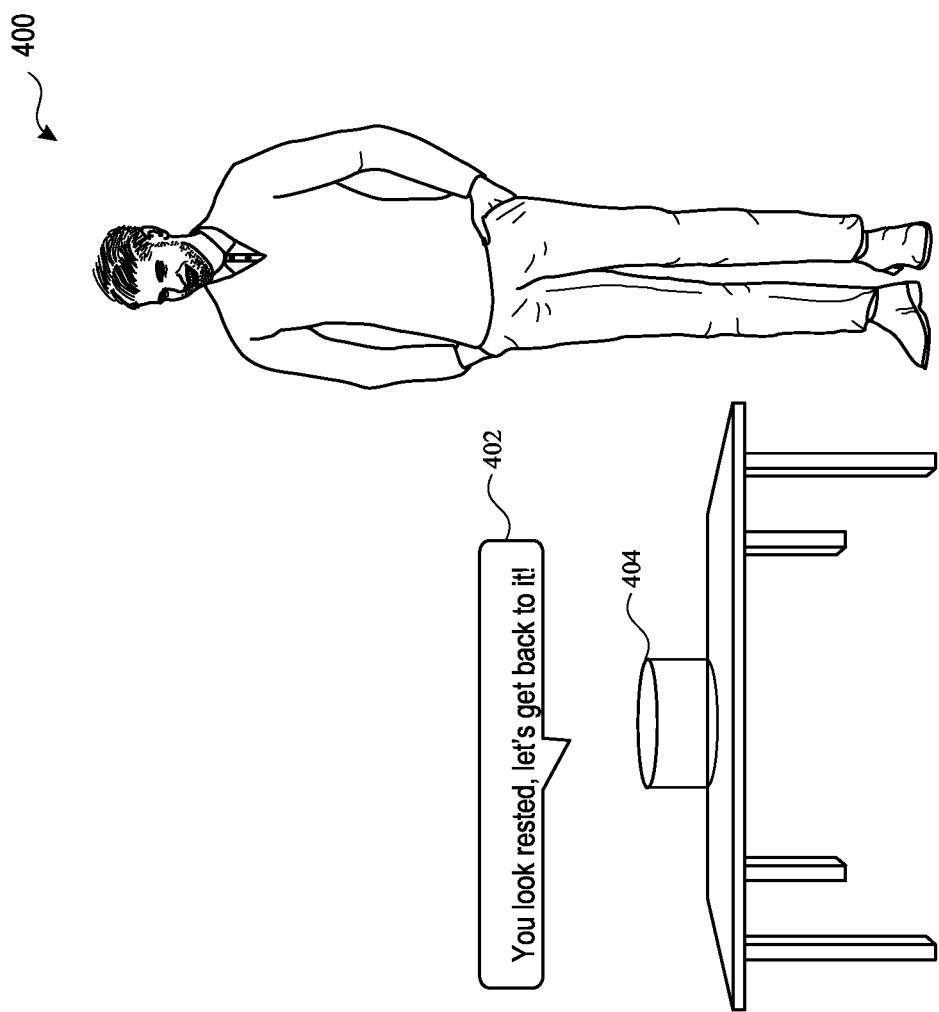
FIG. 4 depicts an exemplary output of the system for monitoring the user wellness level.

In some examples, the second output includes haptic feedback. For example, digital assistant 202 may provide haptic feedback at wearable device 206 to prompt the user to re-engage with VR device 204. In some examples, the second output includes an audio output, as shown in FIG. 4. For example, digital assistant 202 can provide audio prompt 402 "You look rested, let's get back to it!" to the user with one of output devices 208 such as smart speaker 404.

Figure 5:
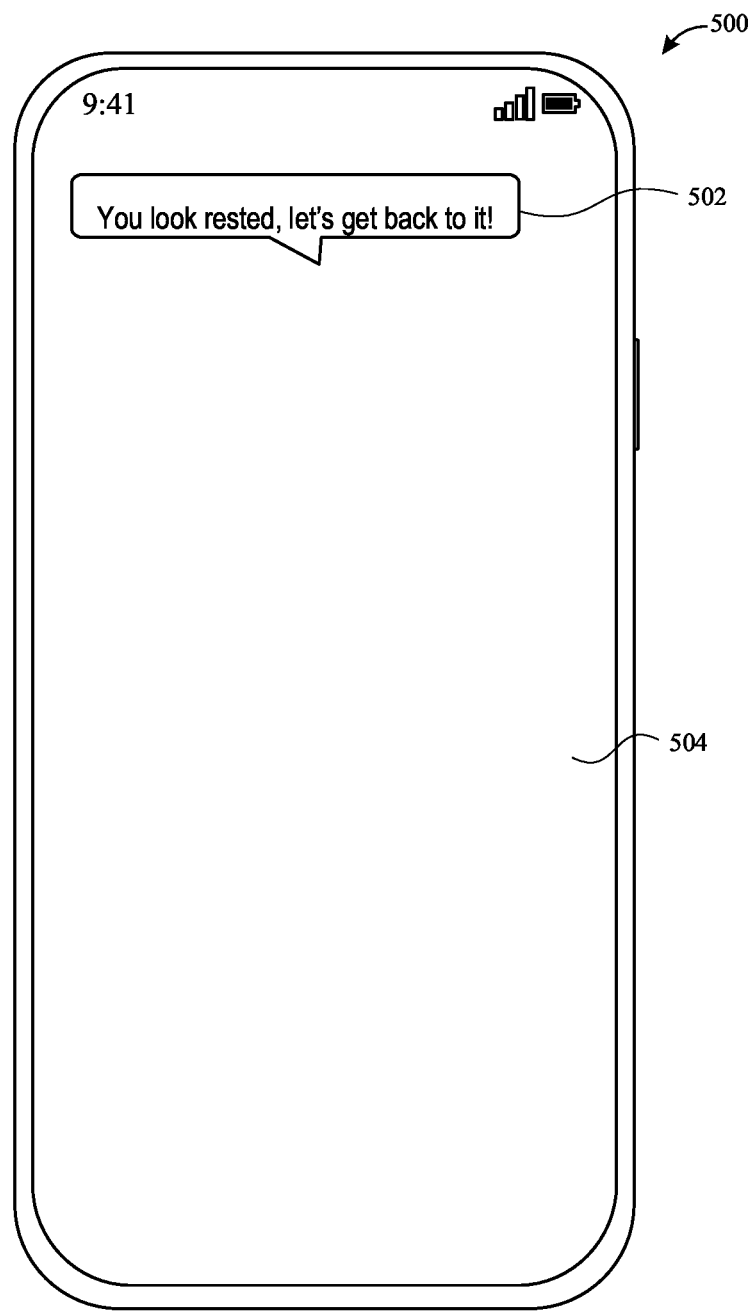
FIG. 5 depicts an exemplary output of the system for monitoring the user wellness level.

In some examples, the second output includes a visual prompt on one of output devices 208, as shown in FIG. 5. For example, digital assistant 202 can provide visual prompt 502 "You look rested, let's get back to it!" to the user on screen 504 of device 500 (e.g., a smart phone or tablet).

It will be understood that system 200 may provide any combination of the outputs discussed above to prompt the user to stop engaging with VR device 204 and then re-engage with VR device 204. Thus, system 200 may provide both haptic feedback and a visual prompt, a visual prompt and an audio prompt, an audio prompt and haptic feedback, or any other combination of the outputs to either prompt the user to stop engaging with VR device 204 or to prompt the user to re-engage with VR device 204.

When digital assistant 202 determines that wellness level 203 is above the predetermined threshold, digital assistant 202 forgoes providing any outputs and continues to provide the virtual environment with VR device 204. In this way the user may continue to use VR device 204 and digital assistant 202 as they would like until the user's wellness level is below the predetermined threshold.

Figure 6:
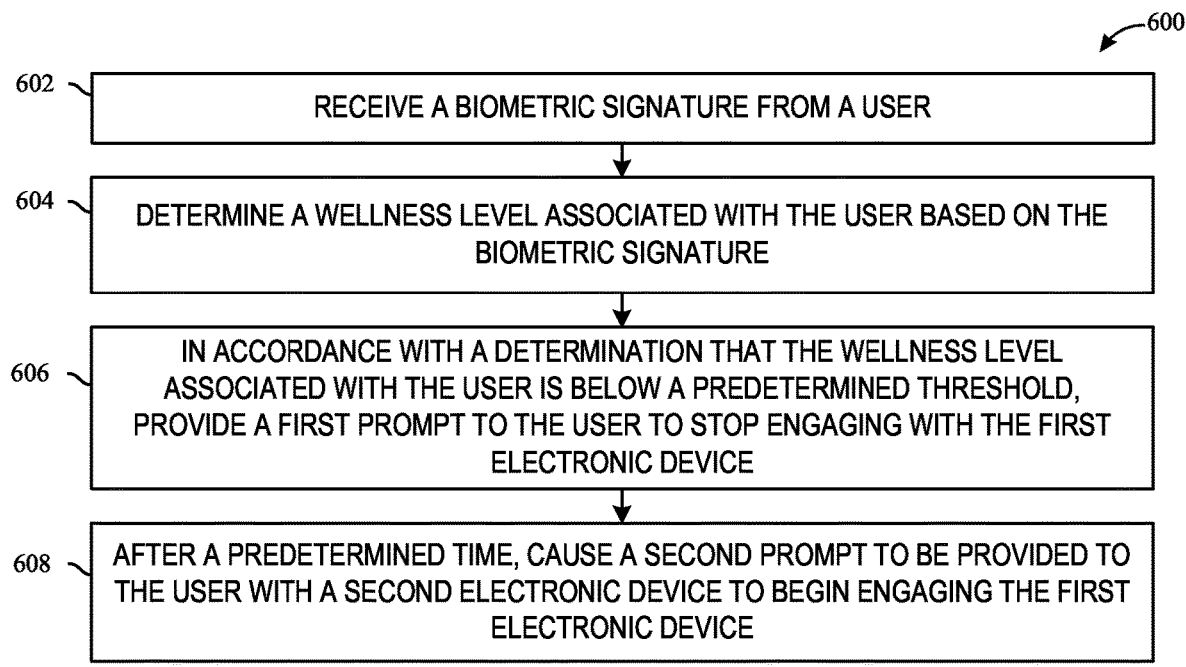
FIG. 6 depicts an exemplary flow diagram illustrating a method for monitoring a user wellness level and providing user suggestions, according to various examples.

FIG. 6 is a flow diagram illustrating a method for monitoring a user wellness level and providing user suggestions, according to various examples. Method 600 is performed at a device (e.g., device 100, 204, 206, 208) with one or more input devices (e.g., a touchscreen, a mic, a camera), and a wireless communication radio (e.g., a Bluetooth connection, WiFi connection, a mobile broadband connection such as a 4G LTE connection). In some embodiments, the electronic device includes a plurality of cameras. In some examples, the device includes one or more biometric sensors which, optionally, include a camera, such as an infrared camera, a thermographic camera, or a combination thereof. Some operations in method 600 are, optionally, combined, the orders of some operations are, optionally, changed, and some operations are, optionally, omitted.

At step 602, a biometric signature (e.g., biometric signature 201) is received from a user. In some examples, the biometric signature includes the pulse of the user, the blood pressure of the user, an attention level of the user, an eye pattern of the user, a facial pattern (e.g., facial expression) of the user, a voice pattern of the user, an EEG of the user, or a temperature of the user.

At step 604, a wellness level (e.g., wellness level 203) associated with the user is determined based on the biometric signature (e.g., biometric signature 201). In some examples, the wellness level includes a score based on the biometric signature received from one or more sensors of the first electronic device (e.g., electronic device 100, VR device 204, wearable device 206, output devices 208). In some examples, the score is based on one or more interactions between the user and the first electronic device.

In some examples, the wellness level (e.g., wellness level 203) associated with the user is based on contextual data associated with the user. In some examples, the contextual data associated with the user includes an amount of time the user has been engaged with the first electronic device (e.g., electronic device 100, VR device 204, wearable device 206, output devices 208). In some examples, the contextual data associated with the user includes one or more scheduled events associated with the user.

In some examples, the wellness level (e.g., wellness level 203) associated with the user is based on contextual data associated with the electronic device (e.g., electronic device 100, VR device 204, wearable device 206, output devices 208). In some examples, the contextual data associated with the first electronic device includes one or more applications open on the first electronic device. In some examples, the contextual data associated with the first electronic device includes a location of the first electronic device. In some examples, the wellness level associated with the user is based on whether a virtual environment (e.g., virtual environment 300) is being provided by the first electronic device.

At step 606, in accordance with a determination that the wellness level associated with the user is below a predetermined threshold, a first output (e.g., prompt 302, 402, 502) to the user to stop engaging with the first electronic device (e.g., electronic device 100, VR device 204, wearable device 206, output devices 208) is provided. In some examples, the first electronic device is capable of producing a virtual environment (e.g., virtual environment 300). In some examples, the predetermined threshold is determined based on one or more baseline biometric signatures (e.g., biometric signature 201) associated with the user. In some examples, the one or more baseline biometric signatures associated with the user are determined based on previous interaction between the user and the first electronic device.

In some examples, the predetermined threshold is determined based on default threshold values. In some examples, the first output (e.g., prompt 302, 402, 502) includes a visual prompt within the virtual environment (e.g., virtual environment 300). In some examples, the first output includes haptic feedback. In some examples, the first output is determined based on one or more user settings.

At step 608, a second output (e.g., prompt 302, 402, 502) is provided to the user with a second electronic device (e.g., electronic device 100, VR device 204, wearable device 206, output devices 208) to begin engaging with the first electronic device (e.g., electronic device 100, VR device 204, wearable device 206, output devices 208) after a predetermined time. In some examples, the predetermined time is based on one or more user settings. In some examples, the predetermined time is based on one or more default settings. In some examples, the second electronic device is a wearable electronic device. In some examples, the first electronic device and the second electronic device are both associated with a user profile for the user. In some examples, the second output is an audio prompt.

As described above, one aspect of the present technology is the gathering and use of data available from various sources to improve the delivery to users of content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates examples in which users selectively block the use of, or access to, personal information data. That is, the present disclosure contemplates that hardware and/or software elements can be provided to prevent or block access to such personal information data. For example, in the case of information delivery services, the present technology can be configured to allow users to select to "opt in" or "opt out" of participation in the collection of personal information data during registration for services or anytime thereafter. In another example, users can select not to provide user information for deliver services. In yet another example, users can select to limit the length of time user information is maintained. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed examples, the present disclosure also contemplates that the various examples can also be implemented without the need for accessing such personal information data. That is, the various examples of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A non-transitory computer-readable storage medium storing one or more programs configured to be executed by one or more processors of a first electronic device, the one or more programs including instructions for:
   receiving a biometric signature of a user while the user is engaging with the first electronic device via one or more sensors associated with the first electronic device;
   determining, based on the biometric signature and contextual data associated with the user, a wellness level associated with the user;
   in accordance with a determination that the wellness level associated with the user is below a predetermined threshold, providing a first output to the user to stop engaging with the first electronic device, wherein the first electronic device is capable of producing a virtual environment; and
   after a predetermined time, causing a second output to be provided to the user with a second electronic device, wherein the second output is related to re-engaging with the first electronic device.

2. The non-transitory computer-readable storage medium of claim 1, wherein the biometric signature includes an attention level of the user.

3. The non-transitory computer-readable storage medium of claim 1, wherein the wellness level includes a score based on the biometric signature received from the one or more sensors of the first electronic device.

4. The non-transitory computer-readable storage medium of claim 3, wherein the score is based on one or more interactions between the user and the first electronic device.

5. The non-transitory computer-readable storage medium of claim 1, wherein the contextual data associated with the user includes an amount of time the user has been engaged with the first electronic device.

6. The non-transitory computer-readable storage medium of claim 1, wherein the contextual data associated with the user includes one or more scheduled events associated with the user.

7. The non-transitory computer-readable storage medium of claim 1, wherein the wellness level associated with the user is based on the contextual data associated with the first electronic device.

8. The non-transitory computer-readable storage medium of claim 7, wherein the contextual data associated with the first electronic device includes one or more applications open on the first electronic device.

9. The non-transitory computer-readable storage medium of claim 7, wherein the contextual data associated with the first electronic device includes a location of the first electronic device.

10. The non-transitory computer-readable storage medium of claim 1, wherein the wellness level associated with the user is based on whether the virtual environment is being provided by the first electronic device.

11. The non-transitory computer-readable storage medium of claim 1, wherein the predetermined threshold is determined based on one or more baseline biometric signatures associated with the user.

12. The non-transitory computer-readable storage medium of claim 11, wherein the one or more baseline biometric signatures associated with the user are determined based on previous interaction between the user and the first electronic device.

13. The non-transitory computer-readable storage medium of claim 1, wherein the predetermined threshold is determined based on default threshold values.

14. The non-transitory computer-readable storage medium of claim 1, wherein the first output includes a visual prompt within the virtual environment.

15. The non-transitory computer-readable storage medium of claim 1, wherein the first output includes haptic feedback.

16. The non-transitory computer-readable storage medium of claim 1, wherein the first output is determined based on one or more user settings.

17. The non-transitory computer-readable storage medium of claim 1, wherein the predetermined time is based on one or more user settings.

18. The non-transitory computer-readable storage medium of claim 1, wherein the predetermined time is based on one or more default settings.

19. The non-transitory computer-readable storage medium of claim 1, wherein the second electronic device is a wearable electronic device.

20. The non-transitory computer-readable storage medium of claim 1, wherein the first electronic device and the second electronic device are both associated with a user profile for the user.

21. The non-transitory computer-readable storage medium of claim 1, wherein the second output is an audio prompt.

22. A first electronic device comprising:
   one or more processors;
   a memory; and
   one or more programs, wherein the one or more programs are stored in the memory and configured to be executed by the one or more processors, the one or more programs including instructions for:
      receiving a biometric signature of a user while the user is engaging with the first electronic device via one or more sensors associated with the first electronic device;
      determining, based on the biometric signature and contextual data associated with the user, a wellness level associated with the user;
      in accordance with a determination that the wellness level associated with the user is below a predetermined threshold, providing a first output to the user to stop engaging with the first electronic device, wherein the first electronic device is capable of producing a virtual environment; and
      after a predetermined time, causing a second output to be provided to the user with a second electronic device, wherein the second output is related to re-engaging with the first electronic device.

23. The first electronic device of claim 22, wherein the biometric signature includes an attention level of the user.

24. The first electronic device of claim 22, wherein the wellness level includes a score based on the biometric signature received from the one or more sensors of the first electronic device.

25. The first electronic device of claim 22, wherein the contextual data associated with the user includes an amount of time the user has been engaged with the first electronic device.

26. The first electronic device of claim 22, wherein the contextual data associated with the user includes one or more scheduled events associated with the user.

27. The first electronic device of claim 22, wherein the wellness level associated with the user is based on the contextual data associated with the first electronic device and wherein the contextual data associated with the first electronic device includes one or more applications open on the first electronic device and/or a location of the first electronic device.

28. The first electronic device of claim 22, wherein the wellness level associated with the user is based on whether the virtual environment is being provided by the first electronic device.

29. The first electronic device of claim 22, wherein the predetermined threshold is determined based on one or more baseline biometric signatures associated with the user.

30. The first electronic device of claim 22, wherein the predetermined threshold is determined based on default threshold values.

31. The first electronic device of claim 22, wherein the first output includes a visual prompt within the virtual environment and/or a haptic feedback and wherein the first output is determined based on one or more user settings.

32. The first electronic device of claim 22, wherein the predetermined time is based on one or more user settings and/or one or more default settings.

33. The first electronic device of claim 22, wherein the second electronic device is a wearable electronic device.

34. The first electronic device of claim 22, wherein the first electronic device and the second electronic device are both associated with a user profile for the user.

35. A method, comprising:
at a first electronic device with one or more processors and memory:
receiving, by the first electronic device, a biometric signature of a user while the user is engaging with the first electronic device via one or more sensors associated with the first electronic device;
determining, by the first electronic device and based on the biometric signature and contextual data associated with the user, a wellness level associated with the user;
in accordance with a determination that the wellness level associated with the user is below a predetermined threshold, providing, by the first electronic device, a first output to the user to stop engaging with the first electronic device, wherein the first electronic device is capable of producing a virtual environment; and
after a predetermined time, causing, by the first electronic device, a second output to be provided to the user with a second electronic device, wherein the second output is related to re-engaging with the first electronic device.

36. The method of claim 35, wherein the biometric signature includes an attention level of the user.

37. The method of claim 35, wherein the wellness level includes a score based on the biometric signature received from the one or more sensors of the first electronic device.

38. The method of claim 35, wherein the contextual data associated with the user includes an amount of time the user has been engaged with the first electronic device.

39. The method of claim 35, wherein the contextual data associated with the user includes one or more scheduled events associated with the user.

40. The method of claim 35, wherein the wellness level associated with the user is based on the contextual data associated with the first electronic device and wherein the contextual data associated with the first electronic device includes one or more applications open on the first electronic device and/or a location of the first electronic device.

41. The method of claim 35, wherein the wellness level associated with the user is based on whether the virtual environment is being provided by the first electronic device.

42. The method of claim 35, wherein the predetermined threshold is determined based on one or more baseline biometric signatures associated with the user.

43. The method of claim 35, wherein the predetermined threshold is determined based on default threshold values.

44. The method of claim 35, wherein the first output includes a visual prompt within the virtual environment and/or a haptic feedback and wherein the first output is determined based on one or more user settings.

45. The method of claim 35, wherein the predetermined time is based on one or more user settings and/or one or more default settings.

46. The method of claim 35, wherein the second electronic device is a wearable electronic device.

47. The method of claim 35, wherein the first electronic device and the second electronic device are both associated with a user profile for the user.

* * * * *